US00PP34138P2

(12) United States Plant Patent
Mathey

(10) Patent No.: US PP34,138 P2
(45) Date of Patent: Apr. 19, 2022

(54) ***DIERVILLA* PLANT NAMED 'SMNDSS'**

(50) Latin Name: ***Diervilla* x *splendens***
Varietal Denomination: SMNDSS

(71) Applicant: Megan M. Mathey, Holland, MI (US)

(72) Inventor: Megan M. Mathey, Holland, MI (US)

(73) Assignee: SPRING MEADOW NURSERY, INC., Grand Haven, MI (US)

( * ) Notice: Subject to any disclaimer, the term of this patent is extended or adjusted under 35 U.S.C. 154(b) by 0 days.

(21) Appl. No.: 17/492,624

(22) Filed: Oct. 3, 2021

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Diervilla* plant named 'SMNDSS', characterized by its upright to outwardly spreading and mounding plant habit; vigorous growth habit and rapid growth rate; freely branching habit; dense and bushy appearance; leaves are bright green in color tinged with greyed orange in the spring and becoming bright yellowish green tinged with reddish orange during the summer and autumn; numerous bright greenish yellow-colored flowers; and good garden performance.

2 Drawing Sheets

Figure 1:
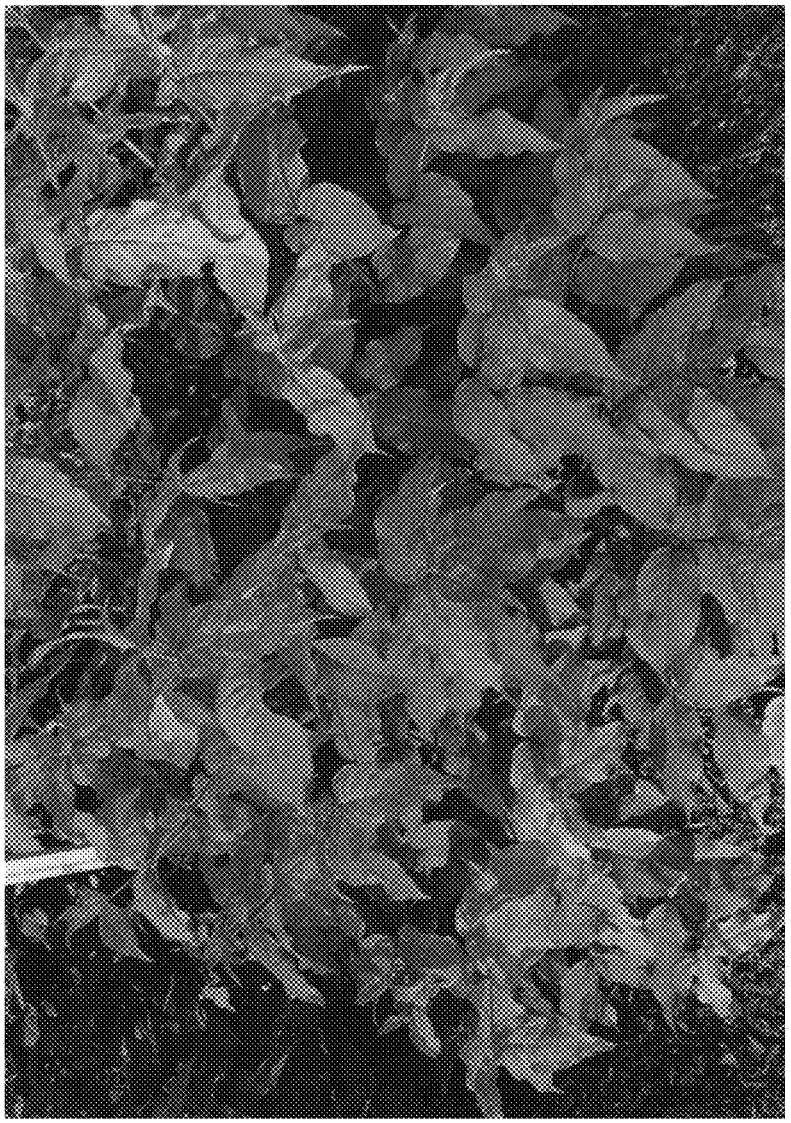

Botanical designation: *Diervilla* x *splendens*.
Cultivar denomination: 'SMNDSS'.

STATEMENT REGARDING PRIOR DISCLOSURES BY INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Diervilla* plant, botanically known as *Diervilla* x *splendens*, commonly referred to as Bush Honeysuckle and hereinafter referred to by the cultivar name 'SMNDSS'.

The new *Diervilla* is a product of a planned breeding program conducted by the Inventor in Grand Haven, Mich. The objective of the breeding program was to develop new freely branching *Diervilla* plants with attractive leaf coloration.

The new *Diervilla* plant originated from an open-pollination during the summer of 2018 in Grand Haven, Mich. of *Diervilla* x *splendens* 'El Madrigal', disclosed in U.S. Plant Pat. No. 28,060, as the female, or seed, parent with an unknown selection of *Diervilla* x *splendens* as the male, or pollen, parent. The new *Diervilla* plant was discovered and selected by the Inventor in 2019 as a single flowering plant within the progeny of the stated open-pollination in a controlled environment in Grand Haven, Mich.

Asexual reproduction of the new *Diervilla* plant by softwood stem cuttings in a controlled greenhouse environment in Grand Haven, Mich. since 2019 has shown that the unique features of this new *Diervilla* plant are stable and reproduced true to type in successive generations of asexual reproduction.

SUMMARY OF THE INVENTION

Plants of the new *Diervilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNDSS'. These characteristics in combination distinguish 'SMNDSS' as a new and distinct *Diervilla* plant:

1. Upright to outwardly spreading and mounding plant habit.
2. Vigorous growth habit and rapid growth rate.
3. Freely branching habit; dense and bushy appearance.
4. Leaves are bright green in color tinged with greyed orange in the spring and becoming bright yellowish green tinged with reddish orange during the summer and autumn.
5. Numerous bright greenish yellow-colored flowers.
6. Good garden performance.

Plants of the new *Diervilla* can be compared to plants of the female parent, 'El Madrigal'. In side-by-side comparisons, plants of the new *Diervilla* differ primarily from plants of 'El Madrigal' in leaf color as leaves of the new *Diervilla* are bright green in color tinged with greyed orange in the spring and becoming bright yellowish green tinged with reddish orange during the summer and autumn whereas leaves of plants of 'El Madrigal' are burgundy to greenish brown in color.

Plants of the new *Diervilla* can also be compared to plants of *Diervilla* x *splendens* 'G2X88544', disclosed in U.S. Plant Pat. No. 27,548. In side-by-side comparisons, plants of the new *Diervilla* differ primarily from plants of 'G2X88544' in leaf color as leaves of the new *Diervilla* are bright green in color tinged with greyed orange in the spring and becoming bright yellowish green tinged with reddish orange during the summer and autumn whereas leaves of plants of 'G2X88544' are orange in color and becoming golden orange in color in the autumn.

BRIEF DESCRIPTION OF THE PHOTOGRAPHS

The accompanying colored photographs illustrate the overall appearance of the new *Diervilla* plant showing the colors as true as it is reasonably possible to obtain in colored reproductions of this type. Colors in the photographs may differ slightly from the color values cited in the detailed botanical description which accurately describe the colors of the new *Diervilla* plant.

The photograph on the first sheet (FIG. 1) is a side perspective view of a typical plant of 'SMNDSS' grown during the spring.

Figure 2:
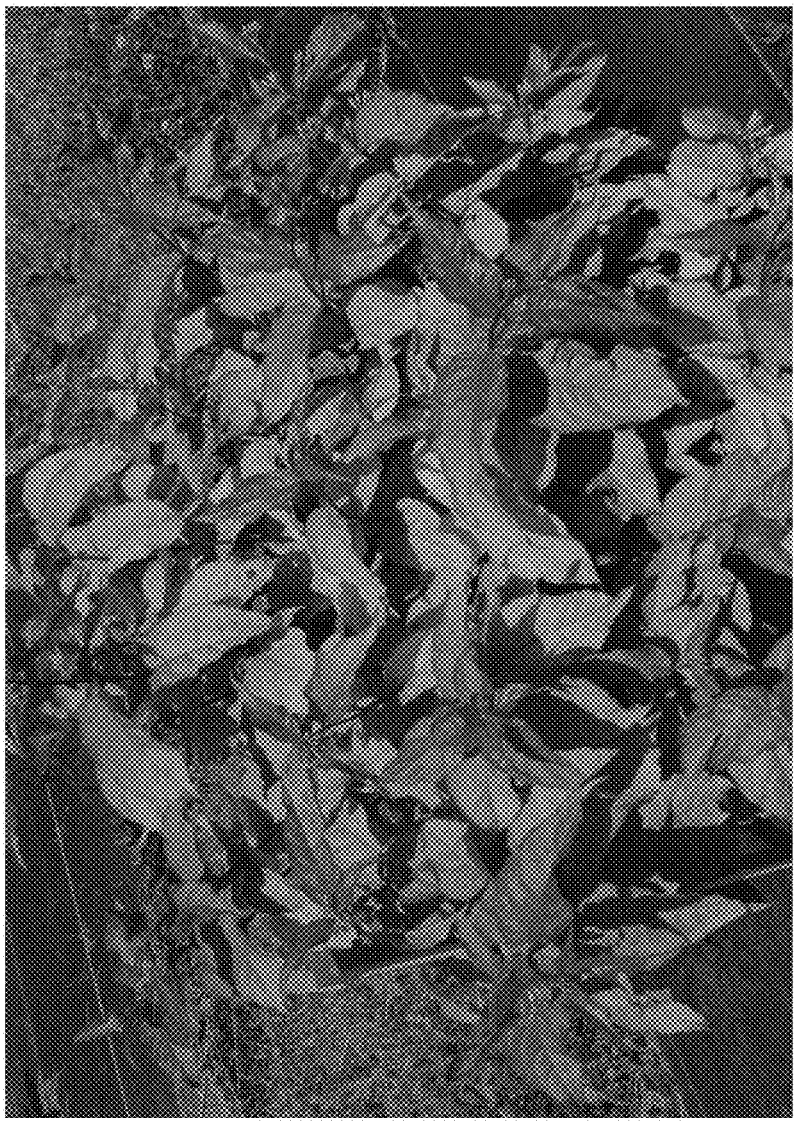

The photograph on the second sheet (FIG. 2) is side perspective view of a typical flowering plant of 'SMNDSS' grown during the summer.

DETAILED BOTANICAL DESCRIPTION

The aforementioned photographs and following observations, measurements and values describe plants grown in the spring and summer in three-gallon containers in a polypropylene-covered shadehouse in Grand Haven, Mich. and under cultural practices typical of commercial *Diervilla* production. During the production of the plants, day temperatures ranged from 18° C. to 27° C. and night temperatures ranged from 5° C. to 10° C. Plants were two years old when the photographs and the description were taken. In the description, color references are made to The Royal Horticultural Society Colour Chart, 2015 Edition, except where general terms of ordinary dictionary significance are used.

Botanical classification: *Diervilla* x *splendens* 'SMNDSS'.

Parentage:

*Female, or seed, parent.*—*Diervilla* x *splendens* 'El Madrigal', disclosed in U.S. Plant Pat. No. 28,060.

*Male, or pollen, parent*.—Unknown selection of *Diervilla* x *splendens*, not patented.

Propagation:

*Type*.—By softwood stem cuttings.

*Time to initiate roots, summer*.—About 10 to 21 days at temperatures about 18° C. to 27° C.

*Time to produce a rooted young plant, summer*.—About four weeks at temperatures about 18° C. to 27° C.

*Root description*.—Medium in thickness to thick; fleshy to fibrous; typically white to tan in color, actual color of the roots is dependent on substrate composition, water quality, fertilizer, substrate temperature and physiological age of roots.

*Rooting habit*.—Moderately freely branching; medium density.

Plant description:

*Plant form and growth habit*.—Perennial deciduous shrub; upright and outwardly spreading and mounding plant habit; with subsequent development, longest stems somewhat drooping; vigorous growth habit and rapid growth rate.

*Branching habit*.—Freely branching habit; about 35 to 40 lateral branches develop per plant; pinching enhances lateral branch development.

*Plant height*.—About 70 cm.

*Plant diameter* (*area of spread*).—About 110 cm.

Lateral branch description:

*Length*.—About 60 cm to 70 cm.

*Diameter*.—About 6 mm.

*Internode length*.—About 4 cm.

*Aspect*.—About 45° to 75° from vertical.

*Strength*.—Strong; somewhat flexible.

*Texture*.—Slightly pubescent on youngest stems; mostly smooth, glabrous; longitudinally ridged.

*Color, developing, upper surface*.—Close to 176A.

*Color, developing, lower surface*.—Close to N144D.

*Color, developed, upper and lower surfaces*.—Close to 199A to 199B.

Leaf description:

*Arrangement*.—Opposite, simple.

*Length*.—About 9 cm to 12 cm.

*Width*.—About 3 cm to 6.5 cm.

*Shape*.—Lanceolate.

*Apex*.—Acuminate.

*Base*.—Obtuse.

*Margin*.—Serrulate.

*Texture, upper surface*.—Smooth, glabrous.

*Texture, lower surface*.—Mostly smooth with ribbing along veins, glabrous.

*Venation pattern*.—Pinnate.

*Color*.—Developing leaves, during spring, upper and lower surfaces: Close to 144B variably overlain with close to between 165A and 166A. Developing leaves, during the summer and autumn, upper and lower surfaces: Close to N144A heavily overlain with close to between 165A and 166A. Fully expanded leaves, during the spring, upper surface: Close to 146A; venation, close to 144C. Fully expanded leaves, during the summer and autumn, upper surface: Close to NN144A to NN144B; proximally, heavily overlain with close to 175B; venation, close to 144C tinged with close to 176A. Fully expanded leaves, during the spring, lower surface: Close to 146B; venation, close to 144C. Fully expanded leaves, during the summer and autumn, lower surface: Close to NN144A to NN144B; proximally, heavily overlain with close to 175B; venation, close to 144C tinged with close to 176A.

*Petioles*.—Length: About 3 mm. Diameter: About 2 mm. Texture, upper and lower surfaces: Smooth, glabrous. Color, during the spring, upper and lower surfaces: Close 144C. Color, during the summer and autumn, upper and lower surfaces: Close 144C tinged with close to 176A.

Flower description:

*Flower appearance and arrangement*.—Salverform flowers arranged in terminal cymes; freely flowering habit with about 30 to 40 flowers per inflorescence with numerous inflorescences developing per plant; flowers face upright to outwardly.

*Fragrance*.—None detected.

*Natural flowering season*.—Plants flower continuously during the early to mid-summer in Michigan; flowers not persistent.

*Inflorescence diameter*.—About 3.5 cm.

*Inflorescence height*.—About 3 cm.

*Flower diameter*.—About 7 mm.

*Flower length*.—About 1.5 cm.

*Flower throat diameter* (*at base of petal lobes*).—About 5 mm.

*Flower tube length*.—About 1 cm.

*Flower tube diameter* (*at base of tube*).—About 2 mm.

*Flower buds*.—Length: About 5 mm to 10 mm. Diameter: About 2 mm. Shape: Oblong. Color: Close to 145A.

*Petals*.—Quantity and arrangement: Five fused with apices free. Length: About 6 mm. Width: About 2 mm. Shape: Oblong. Apex: Obtuse to rounded. Margin: Entire. Texture, upper and lower surfaces: Smooth, silky; glabrous. Color: When opening and fully opened, upper surface: Close to 151C to 151D; flower throat, close to 151C to 151D. When opening and fully opened, lower surface: Close to 151C to 151D; flower tube, close to 151C to 151D.

*Sepals*.—Quantity and arrangement: Five in a single whorl fused at the base. Length: About 3 mm. Width: About 0.5 mm to 1 mm. Shape: Acicular, fine. Apex: Acute. Margin: Entire. Texture, upper and lower surfaces: Smooth, glabrous. Color, upper and lower surfaces: Close to 144B.

*Peduncles*.—Length: About 1.5 cm. Diameter: About 1 mm. Aspect: About 45° to 90° from vertical. Strength: Strong. Texture: Smooth, glabrous. Color, upper and lower surfaces: Close to 144B.

*Pedicels*.—Length: About 8 mm. Diameter: About 1 mm. Aspect: About 45° from peduncle axis. Strength: Strong. Texture: Smooth, glabrous. Color, upper and lower surfaces: Close to 144B tinged with close to 176A.

*Reproductive organs*.—Stamens: Quantity per flower: Five. Filament length: About 1 cm. Filament color: Close to 151D. Anther length: About 4 mm. Anther shape: Lanceolate. Anther color: Close to 160A. Pollen amount: Scarce. Pollen color: Close to 160A. Pistils: Quantity per flower: One. Pistil length: About 1.5 cm. Stigma shape: Round. Stigma color: Close to 146B. Style length: About 1.25 cm. Style color: Close to 151D.

*Fruits and seeds*.—To date, fruit and seed development have not been observed on plants of the new *Diervilla*.

Garden performance: Plants of the new *Diervilla* have been observed to have good garden performance.

Pathogen & pest resistance: To date, plants of the new *Diervilla* have not been shown to be resistant to pathogens and pests common to *Diervilla* plants.

It is claimed:

1. A new and distinct *Diervilla* plant named 'SMNDSS' as illustrated and described.

* * * * *